(12) United States Patent
Candau

(10) Patent No.: US 6,994,844 B2
(45) Date of Patent: Feb. 7, 2006

(54) PHOTOSTABLE UV-SCREENING COMPOSITIONS COMPRISING DIBENZOYLMETHANE/DIARYLBUTADIENE COMPOUNDS

(75) Inventor: Didier Candau, Bièvres (FR)

(73) Assignee: L'OREAL, Paris (FR)

( * ) Notice: Subject to any disclaimer, the term of this patent is extended or adjusted under 35 U.S.C. 154(b) by 146 days.

(21) Appl. No.: 10/463,326

(22) Filed: Jun. 18, 2003

(65) Prior Publication Data

US 2004/0052738 A1    Mar. 18, 2004

Related U.S. Application Data

(63) Continuation of application No. PCT/FR01/03635, filed on Nov. 20, 2001.

(30) Foreign Application Priority Data

Dec. 18, 2000   (FR)   .................... 00 16518

(51) Int. Cl.
*A61K 7/42*   (2006.01)
*A61K 7/44*   (2006.01)
*A61K 7/00*   (2006.01)

(52) U.S. Cl. .................... 424/59; 424/60; 424/400; 424/401

(58) Field of Classification Search .................. 424/59, 424/60, 400, 401
See application file for complete search history.

(56) References Cited

U.S. PATENT DOCUMENTS

| | | | |
|---|---|---|---|
| 4,387,089 A | 6/1983 | De Polo | |
| 4,489,057 A | 12/1984 | Welters et al. | |
| 4,562,067 A | 12/1985 | Hopp et al. | |
| 5,576,354 A | 11/1996 | Deflandre et al. | |
| 6,093,385 A | 7/2000 | Habeck et al. | |
| 6,238,649 B1 | 5/2001 | Habeck et al. | |
| 6,387,355 B2 * | 5/2002 | Heidenfelder et al. | ........ 424/59 |
| 6,391,289 B2 * | 5/2002 | Heidenfelder et al. | ........ 424/59 |
| 6,436,373 B1 | 8/2002 | Habeck et al. | |
| 2002/0001570 A1 | 1/2002 | Heidenfelder et al. | |
| 2002/0004034 A1 | 1/2002 | Heidenfelder et al. | |

FOREIGN PATENT DOCUMENTS

| | | |
|---|---|---|
| DE | 197 46 654 A1 | 2/1999 |
| DE | 197 55 649 A1 | 6/1999 |
| DE | 100 07 017 A1 | 8/2001 |
| EP | 0 114 607 A1 | 8/1984 |
| EP | 0 967 200 A1 | 12/1999 |
| EP | 1 008 586 A1 | 6/2000 |
| EP | 1 133 980 A2 | 9/2001 |
| EP | 1 133 981 A2 | 9/2001 |
| FR | 2 440 933 A1 | 6/1980 |
| FR | 2 326 405 A1 | 4/1987 |
| FR | 2 658 075 A1 | 8/1991 |

* cited by examiner

*Primary Examiner*—Shelley A. Dodson
(74) *Attorney, Agent, or Firm*—Buchanan Ingersoll, P.C.

(57) ABSTRACT

Topically applicable, photostable cosmetic/dermatological UV-screening compositions comprise (a) at least one photolabile UV-screening dibenzoylmethane compound and (b) a dibenzoylmethane photostabilizing amount of at least one 4,4-diarylbutadiene compound, formulated into a topically applicable, cosmetically/dermatologically acceptable support therefor; the weight ratio of the 4,4-diarylbutadiene compound(s) to the diarylbutadiene compound(s) is characteristically greater than 2.5 and the subject compositions are advantageously devoid of any cinnamate sunscreen.

29 Claims, No Drawings

PHOTOSTABLE UV-SCREENING COMPOSITIONS COMPRISING DIBENZOYLMETHANE/DIARYLBUTADIENE COMPOUNDS

CROSS-REFERENCE TO PRIORITY/PCT APPLICATIONS

This application claims priority under 35 U.S.C. § 119 of FR-00/16518, filed Dec. 18, 2000, and is a continuation of PCT/FR01/03635, filed Nov. 20, 2001 and designating the United States (published in the French language on Jun. 27, 2002 as WO 02/49595 A2; the title and abstract were also published in English), both hereby expressly incorporated by reference.

BACKGROUND OF THE INVENTION

1. Technical Field of the Invention

The present invention relates to cosmetic or dermatological compositions for topical application, more particularly in a regime or regimen for photoprotecting the skin and the hair, comprising, in admixture, a UV-screening agent of the dibenzoylmethane derivative type and a 4,4-diarylbutadiene compound.

The present invention also relates to a process for improving the stability towards UV radiation of at least one dibenzoylmethane derivative, which entails combining with said dibenzoylmethane derivative, an effective amount of at least one 4,4-diarylbutadiene compound.

2. Description of Background/Related/Prior Art

It is known that light radiation with wavelengths of between 280 nm and 400 nm permit tanning of the human epidermis and that light rays with wavelengths more particularly between 280 and 320 nm, known as UV-B rays, cause skin burns and erythema which can harm the development of a natural tan. For these reasons, as well as for aesthetic reasons, there is a constant demand for means of controlling this natural tanning in order thus to control the color of the skin; this UV-B radiation should thus be screened out.

It is also known that UV-A rays, with wavelengths between 320 and 400 nm, which cause browning of the skin, are liable to induce adverse changes therein, in particular in the case of sensitive skin or skin which is continually exposed to solar radiation. UV-A rays cause in particular a loss of elasticity of the skin and the appearance of wrinkles leading to premature aging of the skin. They promote triggering of the erythemal reaction or amplify this reaction in certain individuals and may even be the cause of phototoxic or photoallergic reactions. Thus, for aesthetic and cosmetic reasons such as the conservation of the skin's natural elasticity, for example, an increasingly large number of individuals wish to control the effect of UV-A rays on their skin. It is thus desirable also to screen out UV-A radiation.

In this respect, one particularly advantageous family of UV-A screening agents currently consists of dibenzoylmethane derivatives, and in particular 4-tert-butyl-4'-methoxydibenzoylmethane, which have high intrinsic absorbing power. These dibenzoylmethane derivatives, which are products which are now well known per se as screening agents that are active in the UV-A range, are described in particular in FR-A-2-326,405 and FR-A-2-440,933, as well as in EP-A-0-114,607; 4-tert-butyl-4'-methoxydibenzoylmethane is moreover currently sold under the trademark "Parsol 1789" by Hoffmann LaRoche.

Unfortunately, it is found that dibenzoylmethane derivatives are products that are relatively sensitive to ultraviolet radiation (especially UV-A), i.e., more specifically, they have an annoying tendency to degrade more or less quickly under the action of this radiation. Thus, this substantial lack of photochemical stability of dibenzoylmethane derivatives towards ultraviolet radiation, to which they are by nature intended to be subjected, does not make it possible to ensure constant protection during prolonged exposure to sunlight, and as a result repeated applications at regular and close intervals must be made by the user in order to obtain effective protection for the skin against UV rays.

EP-0-967,200, DE-197,46,654, DE-197,55,649, EP-1-008,586, DE-100,07,017, EP-1-133,980 and EP-1-133,981 disclose antisun compositions based on 4,4-diarylbutadienes, which may contain other additional screening agents, such as dibenzoylmethane derivatives.

SUMMARY OF THE INVENTION

It has now unexpectedly and surprisingly been determined that improvedly photostable cosmetic or dermatological compositions for topical application are provided, formulated into a cosmetically acceptable support, which comprise:

(a) at least one UV-screening agent of the dibenzoylmethane derivative type, and (b) at least one 4,4-diarylbutadiene compound; the weight ratio of the 4,4-diarylbutadiene compound to the dibenzoylmethane derivative being greater than 2.5 and said composition advantageously containing no cinnamate sunscreen.

The present invention also features a process for improving the stability towards UV radiation of at least one dibenzoylmethane derivative, which entails combining with said dibenzoylmethane derivative an effective amount of at least one 4,4-diarylbutadiene compound.

DETAILED DESCRIPTION OF BEST MODE AND SPECIFIC/PREFERRED EMBODIMENTS OF THE INVENTION

More particularly, in accordance with the present invention, the expression "effective amount of 4,4-diarylbutadiene" means an amount that is sufficient to obtain an appreciable and significant improvement in the photostability of the dibenzoylmethane derivative or derivatives in the photoprotective cosmetic composition. This minimum amount of photostabilizing agent to be used, which may vary depending on the nature of the cosmetically acceptable support selected for the composition, may be determined without difficulty by means of a standard test for measuring photostability.

Also in accordance with the invention, the term "4,4-diarylbutadiene compound" means any molecule comprising at least one 4,4-diarylbutadiene chromophoric group. This molecule may be in the form of a simple compound, an oligomer or a polymer having, on the chain, grafts comprising the chromophoric group.

Lastly, the present invention also features the use of a 4,4-diarylbutadiene compound for the preparation of a cosmetic or dermatological composition comprising at least one dibenzoylmethane derivative, in order to improve the stability towards UV rays of the said dibenzoylmethane derivative therein.

Other characteristics, aspects, embodiments and advantages of the present invention will become apparent from the detailed description that follows.

Among the preferred 4,4-diarylbutadiene compounds in accordance with the invention that may be selected are the compounds corresponding to formula (I) below:

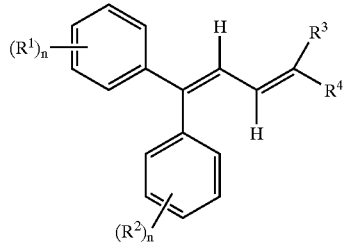

in which the diene system is of Z,Z; Z,E; E,Z or E,E configuration or mixtures of the said configurations, and in which:

$R^1$ and $R^2$, which may be identical or different, denote hydrogen, a linear or branched $C_1$–$C_{20}$ alkyl radical; a $C_2$–$C_{10}$ alkenyl radical; a $C_1$–$C_{12}$ alkoxy radical; a $C_3$–$C_{10}$ cycloalkyl radical; a $C_3$–$C_{10}$ cycloalkenyl radical; a linear or branched $C_1$–$C_{20}$ alkoxycarbonyl radical; a linear or branched $C_1$–$C_{12}$ monoalkylamino radical; a linear or branched $C_1$–$C_{12}$ dialkylamino radical; an aryl radical; a heteroaryl radical or a hydro-solubilizing substituent which comprises a carboxylate group, a sulfonate group or an ammonium residue;

$R^3$ denotes a group $COOR^5$; $COR^5$; $CONR^5R^6$; CN; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; a $C_6$–$C_{18}$ aryl radical; a $C_3$–$C_7$ heteroaryl radical;

$R^4$ denotes a group $COOR^6$; $COR^6$; $CONR^5R^6$; CN; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; an aryl radical; a heteroaryl radical;

$R^5$ and $R^6$, which may be identical or different, denote hydrogen; $[X]_p$—$R^7$; $C_1$–$C_6$-alkylene-$SO_3Y$; $C_1$–$C_6$-alkylene-$PO_3Y$; $C_1$–$C_6$-alkylene-$N(R^8)_3{}^+A^-$; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ bicycloalkenyl radical; a $C_7$–$C_{10}$ cycloalkenyl radical; an aryl radical; a heteroaryl radical;

X denotes a group —$CH_2$—$CH_2$-Z-, —$CH_2CH_2CH_2$Z-, —$CH(CH_3)$—$CH_2$-Z-, —$CH_2$—$CH_2$—$CH_2$—$CH_2$-Z- or —$CH_2$—$CH(CH_2CH_3)$-Z-;

A denotes Cl, Br, I or $SO_4R^9$;

Y denotes hydrogen, $Na^+$, $K^+$, $Mg^{2+}$, $Ca^{2+}$, $Li^+$, $Al^{3+}$ or —$N(R^8)_4{}^+$ Z denotes O or NH;

$R^7$ and $R^8$, which may be identical or different, denote hydrogen, a linear or branched $C_1$–$C_6$ alkyl radical; a linear or branched $C_2$–$C_6$ alkenyl radical; a linear or branched $C_1$–$C_6$ acyl radical;

$R^9$ denotes hydrogen, a linear or branched $C_1$–$C_6$ alkyl radical; a $C_2$–$C_6$ alkenyl radical;

n ranges from 1 to 3;

p ranges from 0 to 150.

Examples of $C_1$–$C_{20}$ alkyl radicals that may be mentioned are: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Examples of $C_2$–$C_{10}$ alkenyl groups that may be mentioned are: ethenyl, n-propenyl, 1-methylethenyl, n-butenyl, 1-methylpropenyl, 2-methylpropenyl, 1,1-dimethylethenyl, n-pentenyl, 1-methylbutenyl, 2-methylbutenyl, 3-methylbutenyl, 2,2-dimethylpropenyl, 1-ethylpropenyl, n-hexenyl, 1,1-dimethylpropenyl, 1,2-dimethylpropenyl, 1-methylpentenyl, 2-methylpentenyl, 3-methylpentenyl, 4-methylpentenyl, 1,1-dimethylbutenyl, 1,2-dimethylbutenyl, 1,3-dimethylbutenyl, 2,2-dimethylbutenyl, 2,3-dimethylbutenyl, 3,3-dimethylbutenyl, 1-ethylbutenyl, 2-ethylbutenyl, 1,1,2-trimethyl-propenyl, 1,2,2-trimethylpropenyl, 1-ethyl-1-methyl-propenyl, 1-ethyl-2-methylpropenyl, n-heptenyl, n-octenyl, n-nonenyl, n-decenyl.

As $C_1$–$C_{12}$ alkoxy radicals, mention may be made of: methoxy, n-propoxy, 1-methylpropoxy, 1-methylethoxy, n-pentoxy, 3-methylbutoxy, 2,2-dimethylpropoxy, 1-methyl-1-ethylpropoxy, octoxy, ethoxy, n-propoxy, n-butoxy, 2-methylpropoxy, 1,1-dimethylpropoxy, hexoxy, heptoxy, 2-ethylhexoxy.

Examples of $C_3$–$C_{10}$ cycloalkyl radicals which may be mentioned are: cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl.

As $C_3$–$C_{10}$ cycloalkenyl radicals containing one or more double bonds, mention may be made of: cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, 1,5-cyclooctadienyl, cyclooctatetraenyl, cyclononenyl or cyclodecenyl.

The cycloalkyl or cycloalkenyl radicals may comprise one or more (preferably from 1 to 3) substituents chosen, for example, from halogen, for instance chlorine, fluorine or bromine; cyano; nitro; amino; $C_1$–$C_4$ alkylamino; $C_1$–$C_4$ dialkylamino; $C_1$–$C_4$ alkyl; $C_1$–$C_4$ alkoxy; hydroxyl; they may also comprise from 1 to 3 hetero atoms, for instance sulfur, oxygen or nitrogen, the free valencies of which may be satisfied with a hydrogen or a $C_1$–$C_4$ alkyl radical.

Examples of acyl radicals that may be mentioned include formyl, acetyl, propionyl and n-butyryl.

The bicycloalkyl or bicycloalkenyl groups are chosen, for example, from bicyclic terpenes, for instance pinane, bornane, pinene, camphor or adamantane derivatives.

The aryl groups are preferably chosen from phenyl and naphthyl rings, which may contain one or more (preferably from 1 to 3) substituents chosen, for example, from halogen, for instance chlorine, fluorine or bromine; cyano; nitro; amino; $C_1$–$C_4$ alkylamino; $C_1$–$C_4$ dialkylamino; $C_1$–$C_4$ alkyl; $C_1$–$C_4$ alkoxy; hydroxyl. Phenyl, methoxy phenyl and naphthyl are more particularly preferred.

The heteroaryl groups generally comprise one or more hetero atoms chosen from sulfur, oxygen and nitrogen.

The hydro-solubilizing groups are, for example, carboxylate or sulfonate groups and more particularly salts thereof with physiologically acceptable cations, for instance the alkali metal salts or trialkylammonium salts such as the tris(hydroxy alkyl)ammonium or 2-methyl-1-propanol-2-ammonium salts. Mention may also be made of ammonium groups, for instance alkylammoniums and forms thereof salified with physiologically acceptable anions.

The preferred compounds of formula (I) are chosen from those of formula (Ia) below:

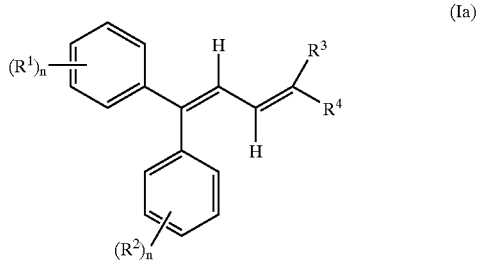

(Ia)

in which the diene system is of Z,Z; Z,E; E,Z or E,E configuration or mixtures of the said configurations, and in which:

$R^1$ and $R^2$, which may be identical or different, denote hydrogen, a $C_1$–$C_8$ alkyl radical; a $C_1$–$C_8$ alkoxy radical; a hydro-solubilizing substituent chosen from a carboxylate group, a sulfonate group and an ammonium residue;

$R^3$ denotes a group $COOR^5$; $CONR^5R^6$; $CN$;

$R^4$ denotes a group $COOR^6$; $CONR^5R^6$;

$R^5$ denotes hydrogen; $[X]_p$—$R^7$; $C_1$–$C_6$ alkylene-$SO_3Y$; $C_1$–$C_6$ alkylene-$N(R^8)_3{}^+A^-$;

$R^6$ denotes $[X]_p$—$R^7$; $C_1$–$C_6$-alkylene-$SO_3Y$; $C_1$–$C_6$ alkylene-$N(R^8)_3{}^+A^-$;

X denotes a —$CH_2$—$CH_2$—O—, —$CH_2CH_2CH_2O$—, —$CH(CH_3)$—$CH_2$—O— group;

A denotes Cl, Br, I or $SO_4R^9$;

Y denotes hydrogen, $Na^+$, $K^+$, $Mg^{2+}$, $Ca^{2+}$, $Li^+$, $Al^{3+}$ or —$N(R^8)_4{}^+$ $R^7$, $R^8$ and $R^9$, which may be identical or different, denote hydrogen or a linear or branched $C_1$–$C_3$ alkyl radical;

n ranges from 1 to 3;

p ranges from 0 to 50.

The compounds of formula (I) that are even more preferred are chosen from those corresponding to formula (Ib) below:

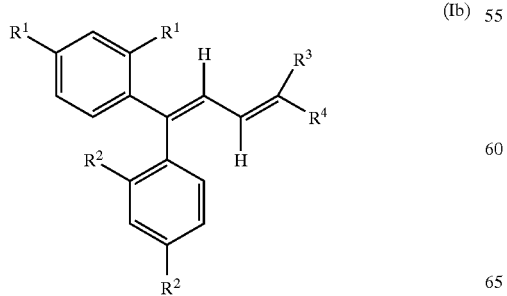

(Ib)

in which the diene system is of Z,Z; Z,E; E,Z or E,E configuration or mixtures of the said configurations, and in which:

$R^1$ and $R^2$, which may be identical or different, denote hydrogen, a $C_1$–$C_8$ alkyl radical; a $C_1$–$C_8$ alkoxy radical;

$R^3$ denotes a group $COOR^5$; $CONR^5R^6$; $CN$;

$R^4$ denotes a group $COOR^6$; $CONR^5R^6$;

$R^5$ denotes hydrogen; $[X]_p$—$R^7$; $C_1$–$C_6$-alkylene-$SO_3Y$; $C_1$–$C_6$-alkylene-$N(R^8)_3{}^+A^-$;

$R^6$ denotes $[X]_p$—$R^7$; $C_1$–$C_6$-alkylene-$SO_3Y$; $C_1$–$C_6$-alkylene-$N(R^8)_3{}^+A^-$;

X denotes a —$CH_2$—$CH_2$—O—, —$CH_2CH_2CH_2O$—, —$CH(CH_3)$—$CH_2$—O— group;

A denotes Cl, Br, I or $SO_4R^9$;

Y denotes hydrogen, $Na^+$, $K^+$, $Mg^{2+}$, $Ca^{2+}$, $Li^+$, $Al^{3+}$ or —$N(R^8)_4{}^+$ $R^7$, $R^8$ and $R^9$, which may be identical or different, denote hydrogen or a linear or branched $C_1$–$C_3$ alkyl radical;

p ranges from 0 to 50.

The compounds of formula (I) that are even more preferred are chosen from those corresponding to formula (Ic) below:

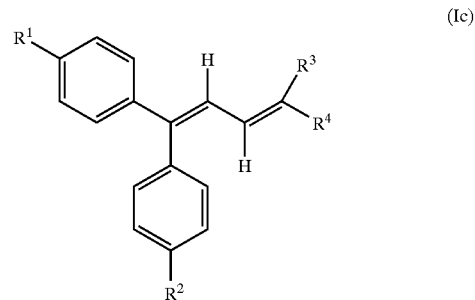

(Ic)

in which the diene system is of Z,Z; Z,E; E,Z or E,E configuration or mixtures of the said configurations, and in which:

$R^1$ and $R^2$, which may be identical or different, denote hydrogen, a $C_1$–$C_8$ alkyl radical; a $C_1$–$C_8$ alkoxy radical;

$R^3$ denotes a group $COOR^5$; $CONR^5R^6$; $CN$;

$R^4$ denotes a group $COOR^6$; $CONR^5R^6$;

$R^5$ denotes hydrogen; $[X]_p$—$R^7$; $C_1$–$C_6$-alkylene-$SO_3Y$; $C_1$–$C_6$-alkylene-$N(R^8)_3{}^+A^-$;

$R^6$ denotes $[X]_p$—$R^7$; $C_1$–$C_6$-alkylene-$SO_3Y$; $C_1$–$C_6$-alkylene-$N(R^8)_3{}^+A^-$;

X denotes a —$CH_2$—$CH_2$—O—, —$CH_2CH_2CH_2O$—, —$CH(CH_3)$—$CH_2$—O— group;

A denotes Cl, Br, I or $SO_4R^9$;

Y denotes hydrogen, $Na^+$, $K^+$, $Mg^{2+}$, $Ca^{2+}$, $Li^+$, $Al^{3+}$ or —$N(R^8)_4{}^+$ $R^7$, $R^8$ and $R^9$, which may be identical or different, denote hydrogen or a linear or branched $C_1$–$C_3$ alkyl radical;

p ranges from 0 to 50.

The compounds of formula (I) that are even more particularly preferred are chosen from the following compounds:

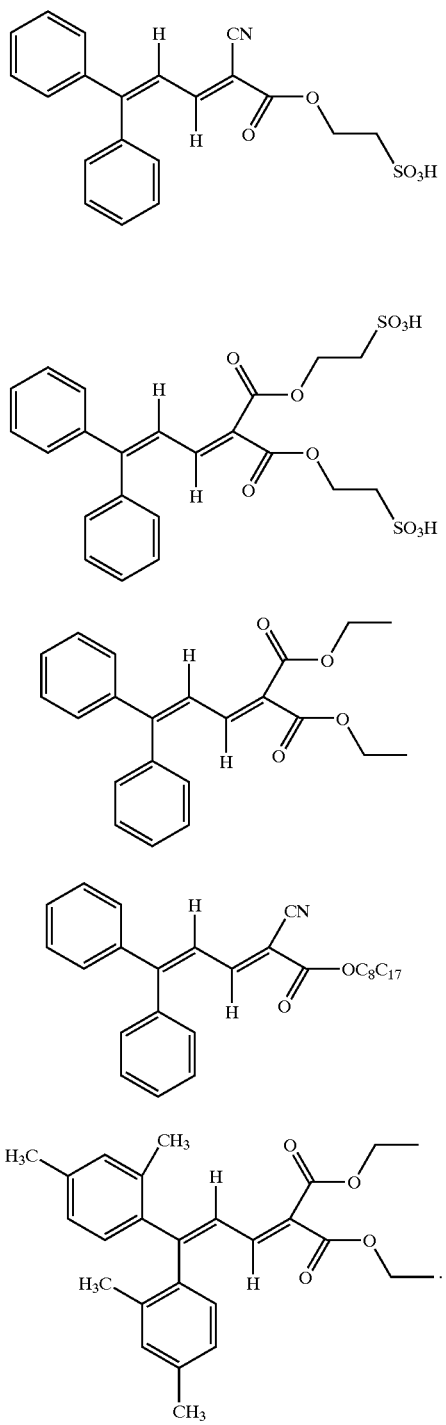

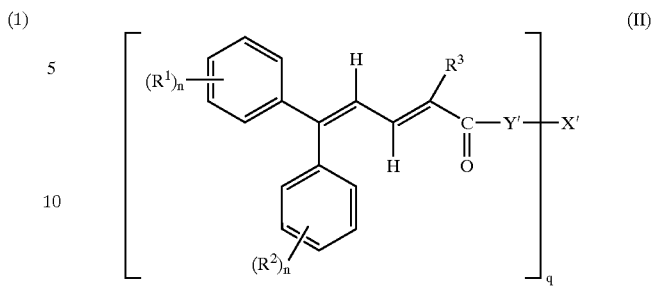

in which the diene system is of Z,Z; Z,E; E,Z or E,E configuration or mixtures of the said configurations, and in which:

$R^1$, $R^2$, $R^3$ and n have the same definitions as in formula (I) above;

Y' denotes a group —O— or —$NR^{10}$—;

$R^{10}$ denotes hydrogen; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; an aryl radical; a heteroaryl radical;

X' denotes an aliphatic or cycloaliphatic linear or branched polyol residue comprising from 2 to 10 hydroxyl groups and of valency q; the carbon-based chain of the said residue optionally being interrupted with one or more sulfur or oxygen atoms; one or more imine groups; one or more $C_1$–$C_4$ alkylimino groups;

q ranges from 2 to 10.

X' is a polyol residue containing from 2 to 10 hydroxyl groups and especially:

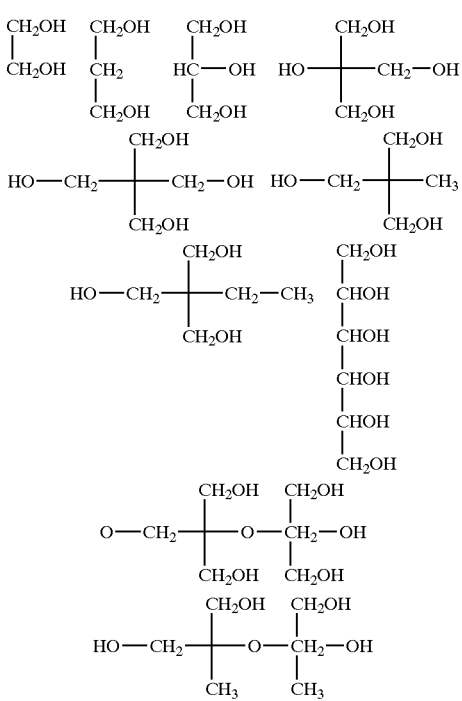

The compounds of formula (I) as defined above are known per se and their structures and syntheses are described in EP-0-967,200, DE-197,46,654 and DE-197,55,649 (which form an integral part of the content of the description).

Among the preferred 4,4-diarylbutadiene compounds in accordance with the invention that may also be mentioned are the oligomers corresponding to formula (II) below:

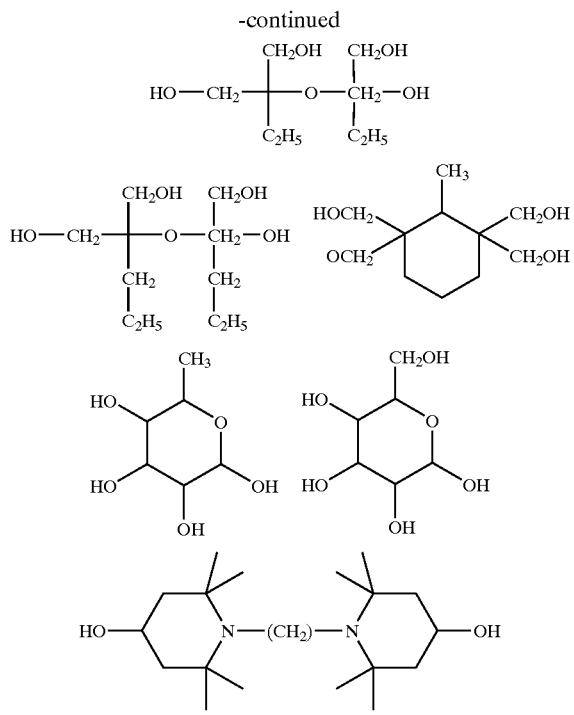

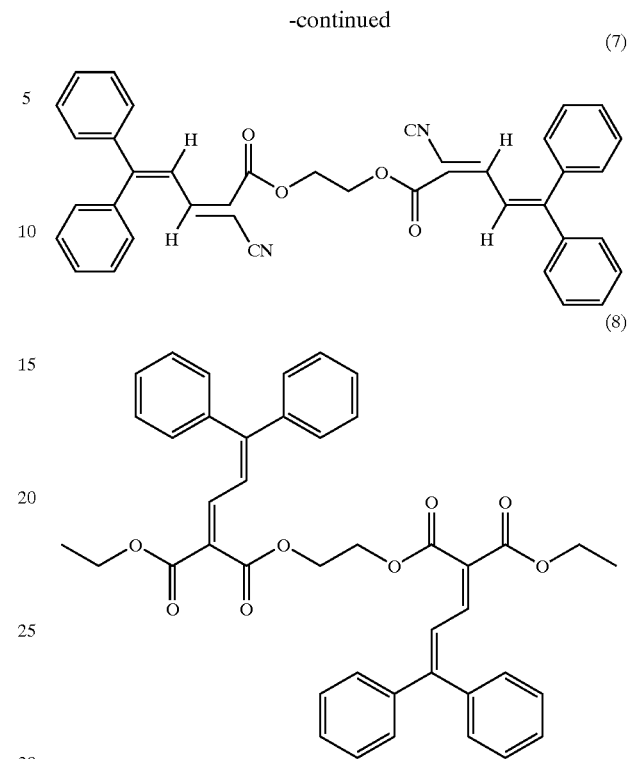

The compounds of formula (II) that are more preferred are those for which:

R¹ and R², which may be identical or different, denote hydrogen, a $C_1$–$C_{12}$ alkyl radical; a $C_1$–$C_8$ alkoxy radical; a hydro-solubilizing substituent chosen from a carboxylate group, a sulfonate group and an ammonium residue;

R³ denotes a group $COOR^5$; $CONR^5R^6$; CN; a $C_3$–$C_{10}$ cycloalkyl radical; a $C_7$–$C_{10}$ bicycloalkyl radical;

R⁵ and R⁶, which may be identical or different, denote a linear or branched $C_1$–$C_{20}$ alkyl radical; a $C_3$–$C_{10}$ cycloalkyl radical; a $C_7$–$C_{10}$ bicycloalkyl radical; optionally substituted naphthyl or phenyl;

X' denotes a polyol residue comprising from 2 to 6 and more particularly from 2 to 4 hydroxyl groups.

The compounds of formula (II) that are even more preferred are those for which:

X' denotes an ethanol or pentaerythrol residue.

The compounds of formula (II) that are even more particularly preferred are chosen from the following compounds:

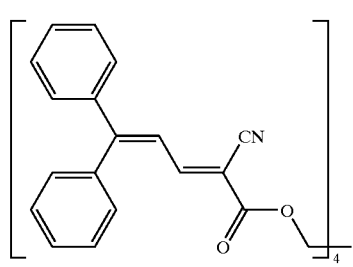

The compounds of formula (II) as defined above are known per se and their structures and syntheses are described in EP-A-1,008,586 (which forms an integral part of the content of the description).

The 4,4-diarylbutadiene compounds in accordance with the invention are preferably present in the composition of the invention in proportions ranging from 0.5% to 15% by weight and more preferably from 1% to 10% by weight, relative to the total weight of the composition.

As mentioned above, the dibenzoylmethane derivatives photostabilized within the scope of the present invention are products that are already well known per se and described in particular in FR-2-326,405, FR-2-440,933 and EP-0-114,607, the teachings of which documents are, as regards the actual definition of these products, entirely included as references in the present description.

According to the present invention, one or more dibenzoylmethane derivatives can of course be used.

Among the dibenzoylmethane derivatives which fall particularly well within the scope of the present invention, mention may be made in particular, in a non-limiting manner, of:

2-methyldibenzoylmethane
4-methyldibenzoylmethane
4-isopropyldibenzoylmethane
4-tert-butyldibenzoylmethane
2,4-dimethyldibenzoylmethane
2,5-dimethyldibenzoylmethane
4,4'-diisopropyldibenzoylmethane
4,4'-dimethoxydibenzoylmethane
4-tert-butyl-4'-methoxydibenzoylmethane
2-methyl-5-isopropyl-4'-methoxydibenzoylmethane
2-methyl-5-tert-butyl-4'-methoxydibenzoylmethane
2,4-dimethyl-4'-methoxydibenzoylmethane
2,6-dimethyl-4-tert-butyl-4'-methoxydibenzoylmethane.

Among the dibenzoylmethane derivatives mentioned above, it is most particularly preferred to use, according to the present invention, 4-(tert-butyl)-4'-methoxydibenzoylmethane, in particular the product sold under the trademark "Parsol 1789" by Hoffmann LaRoche, this screening agent corresponding to the structural formula below:

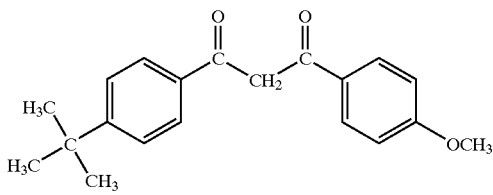

Another dibenzoylmethane derivative which is preferred according to the present invention is 4-isopropyldibenzoylmethane, this screening agent being sold under the name "Eusolex 8020" by Merck and corresponding to the structural formula below:

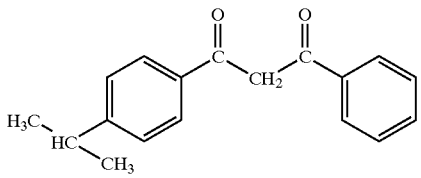

The dibenzoylmethane derivative(s) may be present in the compositions in accordance with the invention in contents ranging from 0.5% to 15% by weight and more particularly from 1% to 10% by weight, relative to the total weight of the composition.

The compositions in accordance with the invention may also comprise other additional organic UV-screening agents that are active in the UVA and/or UVB range (absorbers), which are water-soluble or liposoluble or even insoluble in the cosmetic solvents commonly used.

The additional organic UV-screening agents are especially chosen from anthranilates; salicylic derivatives; camphor derivatives; triazine derivatives such as those described in U.S. Pat. No. 4,367,390, EP-863,145, EP-517,104, EP-570,838, EP-796,851, EP-775,698, EP-878,469 and EP-933,376; benzophenone derivatives; β,β-diphenylacrylate derivatives; benzotriazole derivatives, benzimidazole derivatives; imidazolines; p-aminobenzoic acid (PABA) derivatives; methylenebis(hydroxyphenyl)benzotriazole derivatives as described in U.S. Pat. Nos. 5,237,071, 5,166,355, GB-2-303,549, DE-197-26,184 and EP-893,119; screening polymers and screening silicones such as those described especially in WO 93/04665; dimers derived from α-alkylstyrene, such as those described in DE-198,55,649.

As examples of organic screening agents, mention may be made of the following, denoted herein below under their INCI name:

para-Aminobenzoic Acid Derivatives:
  PABA,
  Ethyl PABA,
  Ethyl dihydroxypropyl PABA,
  Ethylhexyl dimethyl PABA sold in particular under the name "Escalol 507" by ISP,
  Glyceryl PABA,
  PEG-25 PABA sold under the name "Uvinul P25" by BASF.

Salicylic Derivatives:
  Homosalate sold under the name "Eusolex HMS" by Rona/EM Industries,
  Ethylhexyl salicylate sold under the name "Neo Heliopan OS" by Haarmann and Reimer,
  Dipropylene glycol salicylate sold under the name "Dipsal" by Scher,
  TEA salicylate sold under the name "Neo Heliopan TS" by Haarmann and Reimer.

Dibenzoylmethane Derivatives
  Butyl methoxydibenzoylmethane sold in particular under the trademark "Parsol 1789" by Hoffmann LaRoche,
  Isopropyl dibenzoylmethane.

β,β'-Diphenyl Acrylate Derivatives:
  Octocrylene sold in particular under the trademark "Uvinul N539" by BASF,
  Etocrylene sold in particular under the trademark "Uvinal N35" by BASF.

Benzophenone Derivatives:
  Benzophenone-1 sold under the trademark "Uvinul 400" by BASF,
  Benzophenone-2 sold under the trademark "Uvinul D50" by BASF,
  Benzophenone-3 or Oxybenzone sold under the trademark "Uvinul M40" by BASF,
  Benzophenone-4 sold under the trademark "Uvinul MS40" by BASF,
  Benzophenone-5,
  Benzophenone-6 sold under the trademark "Helisorb 11" by Norquay,
  Benzophenone-8 sold under the trademark "Spectra-Sorb UV-24" by American Cyanamid,
  Benzophenone-9 sold under the trademark "Uvinul DS-49" by BASF,
  Benzophenone-12.

Benzylidenecamphor Derivatives:
  3-Benzylidenecamphor manufactured under the name "Mexoryl SD" by Chimex,
  4-Methyl benzylidenecamphor sold under the name "Eusolex 6300" by Merck,
  Benzylidenecamphor sulfonic acid manufactured under the name "Mexoryl SL" by Chimex,
  Camphor benzalkonium methosulfate manufactured under the name "Mexoryl SO" by Chimex,
  Terephthalylidenedicamphorsulfonic acid manufactured under the name "Mexoryl SX" by Chimex,
  Polyacrylamidomethylbenzylidenecamphor manufactured under the name "Mexoryl SW" by Chimex.

Phenyl Benzimidazole Derivatives:
  Phenylbenzimidazolesulfonic acid sold in particular under the trademark "Eusolex 232" by Merck,
  Benzimidazilate sold under the trademark "Neo Heliopan AP" by Haarmann and Reimer.

Triazine Derivatives:
  Anisotriazine sold under the trademark "Tinosorb S" by Ciba Specialty Chemicals
  Ethylhexyl triazone sold in particular under the trademark "Univul T150" by BASF,
  Diethylhexyl butamido triazone sold under the trademark "Uvasorb Heb" by Sigma 3V,
  2,4,6-tris(Diisobutyl 4'-aminobenzalmalonate)s-triazine.

Phenyl Benzotriazole Derivatives:
  Drometrizole trisiloxane sold under the name "Silatrizole" by Rhodia Chimie,
  Methylenebis(benzotriazolyl)tetramethylbutylphenol sold in solid form under the trademark "MIXXIM BB/100" by Fairmount Chemical, or in micronized form as an aqueous dispersion under the trademark "Tinosorb M" by Ciba Specialty Chemicals.

Anthranilic Derivatives:
  Menthyl anthranilate sold under the trademark "Neo Heliopan MA" by Haarmann and Reimer.

Imidazoline Derivatives:
  Ethylhexyldimethoxybenzylidenedioxoimidazoline propionate.

Benzalmalonate Derivatives:
  Polyorganosiloxane containing benzalmalonate functions, sold under the trademark "Parsol SLX" by Hoffmann LaRoche and mixtures thereof.

The organic UV-screening agents that are more particularly preferred are chosen from the following compounds:
  Ethylhexyl salicylate,
  Octocrylene,
  Phenylbenzimidazolesulfonic acid,
  Terephthalylidenedicamphorsulfonic acid,
  Benzophenone-3,
  Benzophenone-4,
  Benzophenone-5,
  4-Methylbenzylidenecamphor,
  Disodium phenyl dibenzimidazole tetrasulfonate,
  Anisotriazine,
  Ethylhexyl triazone,
  Diethylhexyl butamido triazone,
  2,4,6-tris(Diisobutyl 4'-aminobenzalmalonate)-s-triazine,
  Methylenebis(benzotriazolyl)tetramethylbutylphenol,
  Drometrizole trisiloxane, and mixtures thereof.

The cosmetic compositions according to the invention may also comprise pigments or nanopigments (average size of the primary particles: generally between 5 nm and 100 nm and preferably between 10 nm and 50 nm) of coated or uncoated metal oxides, such as, for example, nanopigments of titanium oxide (amorphous or crystallized in rutile and/or anatase form), of iron oxide, of zinc oxide, of zirconium oxide or of cerium oxide, which are all UV photoprotective agents that are well known per se. Standard coating agents are, moreover, alumina and/or aluminum stearate. Such coated or uncoated metal oxide nanopigments are described in particular in EP-A-0-518,772 and EP-A-0-518,773.

The compositions according to the invention may also contain agents for artificially tanning and/or browning the skin (self-tanning agents) such as, for example, dihydroxyacetone (DHA).

The compositions of the invention may also comprise standard cosmetic adjuvants and additives chosen especially from fatty substances, organic solvents, ionic or nonionic thickeners, softeners, antioxidants, free-radical scavengers, opacifiers, stabilizers, emollients, silicones, α-hydroxy acids, antifoams, moisturizers, vitamins, insect repellants, fragrances, preserving agents, surfactants, anti-inflammatories, substance P antagonists, fillers, polymers, propellants, acidifying or basifying agents, colorants or any other ingredient usually used in cosmetics, in particular for the manufacture of antisun compositions in the form of emulsions.

The fatty substances may consist of an oil or a wax or mixtures thereof. The term "oil" means a compound that is liquid at room temperature. The term "wax" means a compound that is solid or substantially solid at room temperature, and whose melting point is generally above 35° C. They also comprise linear or cyclic fatty acids, fatty alcohols and fatty acid esters such as benzoic acid, trimellitic acid and hydroxybenzoic acid derivatives.

Oils that may be mentioned include mineral oils (paraffin); plant oils (sweet almond oil, macadamia oil, blackcurrant pip oil or jojoba oil); synthetic oils, for instance perhydrosqualene, fatty alcohols, fatty acids or fatty esters (for instance the $C_{12}$–$C_{15}$ alkyl benzoates sold under the trademark "Finsolv TN" by Finetex, octyl palmitate, isopropyl lanolate, triglycerides including capric/caprylic acid triglycerides), oxyethylenated or oxypropylenated fatty esters and ethers; silicone oils (cyclomethicone, and polydimethylsiloxanes or PDMS) or fluoro oils, and polyalkylenes.

Waxy compounds that may be mentioned include paraffin, carnauba wax, beeswax and hydrogenated castor oil.

Among the organic solvents that may be mentioned are lower alcohols and polyols.

Nonetheless, a person skilled in the art will take care to select this or these optional additional compound(s) and/or the amounts thereof such that the advantageous properties, in particular the photostability, intrinsically associated with the compositions in accordance with the invention are not, or are not substantially, adversely affected by the envisaged addition(s).

The compositions of the invention may be prepared according to techniques that are well known to those skilled in the art, in particular those intended for preparing emulsions of oil-in-water or water-in-oil type.

These compositions may be in particular in the form of a simple emulsion or a complex emulsion (O/W, W/O, O/W/O or W/O/W), such as a cream, a milk, a gel or a cream-gel; a powder or a solid tube, and may optionally be packaged as an aerosol and may be in the form of a mousse or spray.

When it is an emulsion, the aqueous phase of this emulsion may comprise a nonionic vesicular dispersion prepared according to known processes (Bangham, Standish and Watkins, J. Mol. Biol. 13, 238 (1965), FR-2-315,991 and FR-2-416,008).

The cosmetic composition of the invention may be topically applied as a composition for protecting the human epidermis or the hair against ultraviolet rays, as an antisun composition or as a makeup product.

When the cosmetic composition according to the invention is administered in a regime or regimen for protecting the human epidermis against UV rays, or as an antisun composition, it may be in the form of a suspension or a dispersion in solvents or fatty substances, in the form of a nonionic vesicular dispersion or in the form of an emulsion, preferably of oil-in-water type, such as a milk or a cream, or in the form of an ointment, a gel, a cream-gel, a solid tube, a powder, a stick, an aerosol mousse or a spray.

When the cosmetic composition according to the invention is employed for protecting the hair against UV rays, it may be in the form of a shampoo, a lotion, a gel, an emulsion or a nonionic vesicular dispersion and may constitute, for example, a rinse-out composition, to be applied before or after shampooing, before or after dyeing or bleaching, or before, during or after permanent-waving or straightening the hair, a styling or treating lotion or gel, a blow-drying or hairsetting lotion or gel, or a permanent-waving, straightening, dyeing or bleaching composition for the hair.

When the composition is used as a makeup product for the eyelashes, the eyebrows or the skin, such as an epidermal treatment cream, a foundation, a tube of lipstick, an eyeshadow, a face powder, mascara or an eyeliner, it may be in solid or pasty, anhydrous or aqueous form, for instance oil-in-water or water-in-oil emulsions, nonionic vesicular dispersions or suspensions.

As a guide, for the antisun formulations in accordance with the invention that contain a support of oil-in-water emulsion type, the aqueous phase (especially comprising the hydrophilic screening agents) generally represents from 50% to 95% by weight and preferably from 70% to 90% by weight, relative to the total weight of the formulation, the oily phase (especially comprising the lipophilic screening agents) from 5% to 50% by weight and preferably from 10% to 30% by weight, relative to the total weight of the formulation, and the (co)emulsifier(s) from 0.5% to 20% by weight and preferably from 2% to 10% by weight, relative to the total weight of the formulation.

As indicated above, the present invention features the use of a composition as defined above for the manufacture of a cosmetic or dermatological composition suited for protecting the skin and/or the hair against ultraviolet radiation, in particular solar radiation.

The present invention also features a process for improving the stability of at least one dibenzoylmethane derivative towards UV radiation, which entails combining with said dibenzoylmethane derivative, an effective amount of at least one 4,4-diarylbutadiene as defined above.

This invention also features the use of a UV-screening agent of the 4,4-diarylbutadiene type as defined above in the preparation of a cosmetic or dermatological composition comprising at least one UV-screening agent of the dibenzoylmethane derivative type, with the objective of improving the stability of said dibenzoylmethane derivative towards UV rays.

In order to further illustrate the present invention and the advantages thereof, the following specific examples are given, it being understood that same are intended only as illustrative and in nowise limitative.

In said examples to follow, all parts and percentages are given by weight, unless otherwise indicated.

The following Tables 1 and 2 report Examples 1 and 2, specific compositions according to the invention.

TABLE 1

| COMPOSITION | EXAMPLE 1 |
| --- | --- |
| Glyceryl mono/distearate/polyethylene glycol stearate (100 EO) mixture (Arlacel 165 FL-ICI) | 2 |
| Stearyl alcohol (Lanette 18-Henkel) | 1 |
| Stearic acid from palm oil (Stearine TP-Stearinic Dubois) | 2.5 |
| Polydimethylsiloxane (Dow Corning 200 Fluid-Dow Corning) | 0.5 |
| C12/C15 alkyl benzoate (Witconol TN-WITCO) | 20 |
| Triethanolamine | 0.5 |
| Butylmethoxydibenzoylmethane (Parsol 1789-Hoffmann LaRoche) | 2 |
| Compound of formula (1) | 8 |
| Glycerol | 4 |
| Triethanolamine | 0.3 |
| Polyacrylic acid (Synthalen K-3V) | 0.4 |
| Preserving agents | qs |
| Demineralized water qs | 100 g |

TABLE 2

| COMPOSITION | EXAMPLE 2 |
| --- | --- |
| Glyceryl mono/distearate/polyethylene glycol stearate (100 EO) mixture (Arlacel 165 FL-ICI) | 2 |
| Stearyl alcohol (Lanette 18-Henkel) | 1 |
| Stearic acid from palm oil (Stearine TP-Stearinerie Dubois) | 2.5 |
| Polydimethylsiloxane (Dow Corning 200 Fluid-Dow Corning) | 0.5 |
| C12/C15 alkyl benzoate (Witconol TN-WITCO) | 20 |
| Triethanolamine | 0.5 |
| Butylmethoxydibenzoylmethane (Parsol 1789-Hoffmann LaRoche) | 2 |
| Compound of formula (6) | 8 |
| Glycerol | 4 |
| Triethanolamine | 0.3 |
| Polyacrylic acid (Synthalen K-3V) | 0.4 |
| Preserving agents | qs |
| Demineralized water qs | 100 g |

Each patent, patent application and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable, photostable cosmetic/dermatological UV-screening composition, comprising:
    (a) at least one UV-screening dibenzoylmethane compound and
    (b) a dibenzoylmethane photostabilizing amount of at least one 4,4-diarylbutadiene compound, formulated into a topically applicable, cosmetically/dermatologically acceptable support therefor;
    the weight ratio of said at least one diarylbutadiene compound to said at least one dibenzoylmethane compound being greater than 2.5 and said composition being devoid of any cinnamate sunscreen.

2. The photostable cosmetic/dermatological composition as defined by claim 1, said at least one diarylbutadiene compound having the formula (I) below:

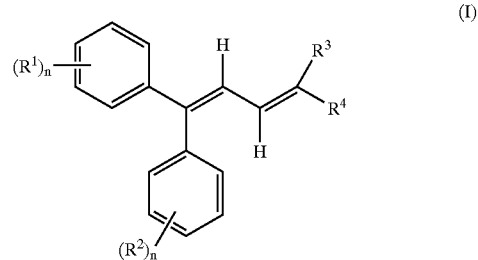

in which the diene system is of Z,Z; Z,E; E,Z or E,E configuration or a mixture of said configurations, and in which the radicals $R^1$ and $R^2$, which are identical or different, are each hydrogen, a linear or branched $C_1$–$C_{20}$ alkyl radical; a $C_2$–$C_{10}$ alkenyl radical; a $C_1$–$C_{12}$ alkoxy radical; a $C_3$–$C_{10}$ cycloalkyl radical; a $C_3$–$C_{10}$ cycloalkenyl radical;

a linear or branched $C_1$–$C_{20}$ alkoxycarbonyl radical; a linear or branched $C_1$–$C_{12}$ monoalkylamino radical; a linear or branched $C_1$–$C_{12}$ dialkylamino radical; an aryl radical; a heteroaryl radical or a hydro-solubilizing substituent which comprises a carboxylate group, a sulfonate group or an ammonium residue; $R^3$ is a group $COOR^5$; $COR^5$; $CONR^5R^6$; CN; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; a $C_6$–$C_{18}$ aryl radical; a $C_3$–$C_7$ heteroaryl radical; $R^4$ is a group $COOR^6$; $COR^6$; $CONR^5R^6$; CN; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; an aryl radical; a heteroaryl radical; the radicals $R^5$ and $R^6$, which are identical or different, are each hydrogen; $[X]_p$—$R^7$; $C_1$–$C_6$-alkylene-$SO_3Y$; $C_1$–$C_6$-alkylene-$PO_3Y$; $C_1$–$C_6$-alkylene-$N(R^8)_3{}^+A^-$; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; an aryl radical; a heteroaryl radical; X is a group —$CH_2$—$CH_2$-Z-, —$CH_2CH_2CH_2$-Z-, —$CH(CH_3)$—$CH_2$-Z-, —$CH_2$—$CH_2$—$CH_2$-Z- or —$CH_2$—CH($CH_2CH_3$)-Z-; A is Cl, Br, I or $SO_4R^9$; Y is hydrogen, $Na^+$, $K^+$, $Mg^{2+}$, $Ca^{2+}$, $Li^+$, $Al^{3+}$ or —$N(R^8)_4{}^+$; Z is O or NH; the radicals $R^7$ and $R^8$, which are identical or different, are each hydrogen, a linear or branched $C_1$–$C_6$ alkyl radical; a linear or branched $C_2$–$C_6$ alkenyl radical; a linear or branched $C_2$–$C_6$ acyl radical; $R^9$ is hydrogen, a linear or branched $C_1$–$C_6$ alkyl radical; a $C_2$–$C_6$ alkenyl radical; n ranges from 1 to 3; and p ranges from 0 to 150.

3. The photostable cosmetic/dermatological composition as defined by claim 2, in which the compound of formula (I) has the formula (Ia) below:

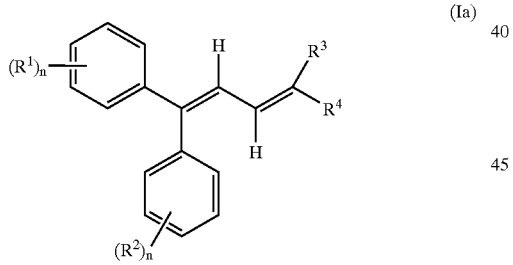

(Ia)

in which the diene system is of Z,Z; Z,E; E,Z or E,E configuration or a mixture of said configurations, and in which the radicals $R^1$ and $R^2$, which are identical or different, are each hydrogen, a $C_1$–$C_8$ alkyl radical; a $C_1$–$C_8$ alkoxy radical; a hydro-solubilizing substituent which comprises a carboxylate group, a sulfonate group or an ammonium residue; $R^3$ is a group $COOR^5$; $CONR^5R^6$; CN; $R^4$ is a group $COOR^6$; $CONR^5R^6$; $R^5$ is hydrogen; $[X]_p$—$R^7$; $C_1$–$C_6$-alkylene-$SO_3Y$; $C_1$–$C_6$-alkylene-$N(R^8)_3{}^+A^-$; $R^6$ is $[X]_p$—$R^7$; $C_1$–$C_6$-alkylene-$SO_3Y$; $C_1$–$C_6$-alkylene-$N(R^8)_3{}^+A^-$; X is a —$CH_2$—$CH_2$—O—, —$CH_2CH_2CH_2O$—, —$CH(CH_3)$—$CH_2$—O— group; A is Cl, Br, I or $SO_4R^9$; Y is hydrogen, $Na^+$, $K^+$, $Mg^{2+}$, $Ca^{2+}$, $Li^+$, $Al^{3+}$ or —$N(R^8)_4{}^+$; the radicals $R^7$, $R^8$ and $R^9$, which are identical or different, are each hydrogen or a linear or branched $C_1$–$C_3$ alkyl radical; n ranges from 1 to 3; and p ranges from 0 to 50.

4. The photostable cosmetic/dermatological composition as defined by claim 2, in which the compound of formula (I) has the formula (Ib) as below:

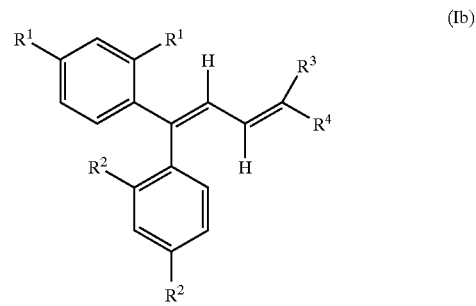

(Ib)

in which the diene system is of Z,Z; Z,E; E,Z or E,E configuration or a mixture of said configurations, and in which the radicals $R^1$ and $R^2$, which are identical or different, are each hydrogen, a $C_1$–$C_8$ alkyl radical; a $C_1$–$C_8$ alkoxy radical; $R^3$ is a group $COOR^5$; $CONR^5R^6$; CN; $R^4$ is a group $COOR^6$; $CONR^5R^6$; $R^5$ is hydrogen; $[X]_p$—$R^7$; $C_1$–$C_6$-alkylene-$SO_3Y$; $C_1$–$C_6$-alkylene-$N(R^8)_3{}^+A^-$; $R^6$ is $[X]_p$—$R^7$; $C_1$–$C_6$-alkylene-$SO_3Y$; $C_1$–$C_6$-alkylene-$N(R^8)_3{}^+A^-$; X is a —$CH_2$—$CH_2$—O—, —$CH_2CH_2CH_2O$—, —$CH(CH_3)$—$CH_2$—O— group; A is Cl, Br, I or $SO_4R^9$; Y is hydrogen, $Na^+$, $K^+$, $Mg^{2+}$, $Ca^{2+}$, $Li^+$, $Al^{3+}$ or —$N(R^8)_4{}^+$; the radicals $R^7$, $R^8$ and $R^9$, which are identical or different, are each hydrogen or a linear or branched $C_1$–$C_3$ alkyl radical; and p ranges from 0 to 50.

5. The photostable cosmetic/dermatological composition as defined by claim 2, in which the compound of formula (I) has the formula (Ic) below:

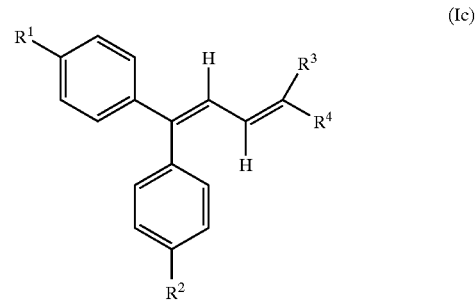

(Ic)

in which the diene system is of Z,Z; Z,E; E,Z or E,E configuration or a mixture of said configurations, and in which the radicals $R^1$ and $R^2$, which are identical or different, are each hydrogen, a $C_1$–$C_8$ alkyl radical; a $C_1$–$C_8$ alkoxy radical; $R^3$ is a group $COOR^5$; $CONR^5R^6$; CN; $R^4$ is a group $COOR^6$; $CONR^5R^6$; $R^5$ is hydrogen; $[X]_p$—$R^7$; $C_1$–$C_6$-alkylene-$SO_3Y$; $C_1$–$C_6$-alkylene-$N(R^8)_3{}^+A^-$; $R^6$ is $[X]_p$—$R^7$; $C_1$–$C_6$-alkylene-$SO_3Y$; $C_1$–$C_6$-alkylene-$N(R^8)_3{}^+A^-$; X is a —$CH_2$—$CH_2$—O—, —$CH_2CH_2CH_2O$—, —$CH(CH_3)$—$CH_2$—O— group; A is Cl, Br, I or $SO_4R^9$; Y is hydrogen, $Na^+$, $K^+$, $Mg^{2+}$, $Ca^{2+}$, $Li^+$, $Al^{3+}$ or —$N(R^8)_4{}^+$; the radicals $R^7$, $R^8$ and $R^9$, which are identical or different, are each hydrogen or a linear or branched $C_1$–$C_3$ alkyl radical; and p ranges from 0 to 50.

6. The photostable cosmetic/dermatological composition as defined by claim 2, in which the compound of formula (I) is selected from among the following compounds:

(1)

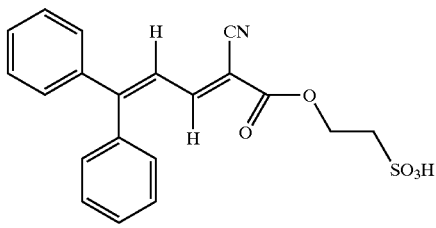

(2)

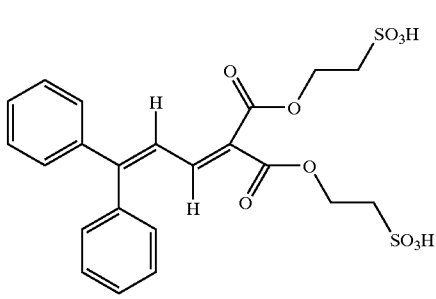

(3)

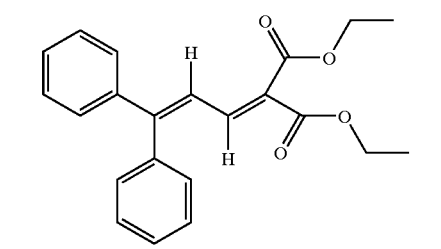

(4)

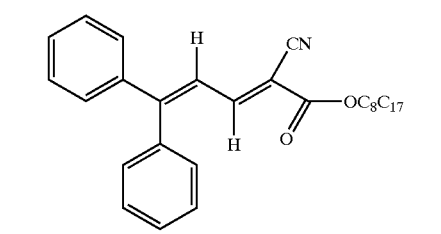

(5)

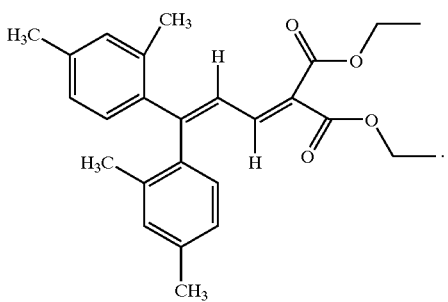

7. The photostable cosmetic/dermatological composition as defined by claim 1, said at least one 4,4-diarylbutadiene compound comprising an oligomer having the formula (II) below:

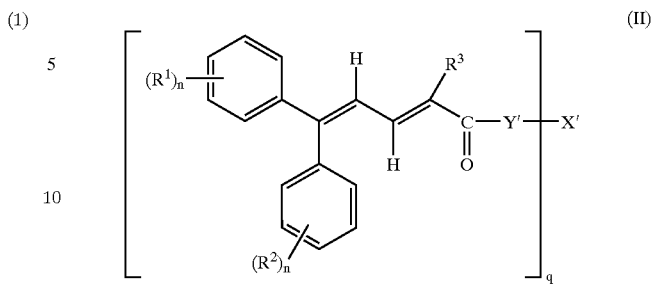

in which the diene system is of Z,Z; Z,E; E,Z or E,E configuration or a mixture of said configurations, and in which $R^1$, $R^2$, $R^3$ and n have the same definitions as in formula (I); Y' is a group —O— or —$NR^{10}$—; $R^{10}$ is hydrogen; a linear or branched $C_1$–$C_{20}$ alkyl radical; a $C_2$–$C_{10}$ alkenyl radical; a $C_3$–$C_{10}$ cycloalkyl radical; a $C_7$–$C_{10}$ bicycloalkyl radical; a $C_3$–$C_{10}$ cycloalkenyl radical; a $C_7$–$C_{10}$ bicycloalkenyl radical; an aryl radical; a heteroaryl radical; X' is an aliphatic or cycloaliphatic linear or branched polyol residue having from 2 to 10 hydroxyl groups and of valency q; the carbon-based chain of said residue optionally being interrupted with one or more sulfur or oxygen atoms; one or more imine groups or one or more $C_1$–$C_4$ alkylimino groups; and q ranges from 2 to 10.

8. The photostable cosmetic/dermatological composition as defined by claim 7, wherein the oligomer of formula (II), the radicals $R^1$ and $R^2$, which are identical or different, are each hydrogen, a $C_1$–$C_{12}$ alkyl radical; a $C_1$–$C_8$ alkoxy radical; a hydro-solubilizing substituent which comprises a carboxylate group, a sulfonate group or an ammonium residue; $R^3$ is a group $COOR^5$; $CONR^5R^6$; CN; a $C_3$–$C_{10}$ cycloalkyl radical; a $C_7$–$C_{10}$ bicycloalkyl radical; the radials $R^5$ and $R^6$, which are identical or different, are each a linear or branched $C_1$–$C_{20}$ alkyl radical; a $C_3$–$C_{10}$ cycloalkyl radical; a $C_7$–$C_{10}$ bicycloalkyl radical; or an optionally substituted naphthyl or phenyl; and X' is a polyol residue having from 2 to 6 hydroxyl groups.

9. The photostable cosmetic/dermatological composition as defined by claim 8, wherein said compound of formula (II), X' is an ethanol or pentaerythrol residue.

10. The photostable cosmetic/dermatological composition as defined by claim 7, said at least one oligomer of formula (II) comprising at least one of:

(6)

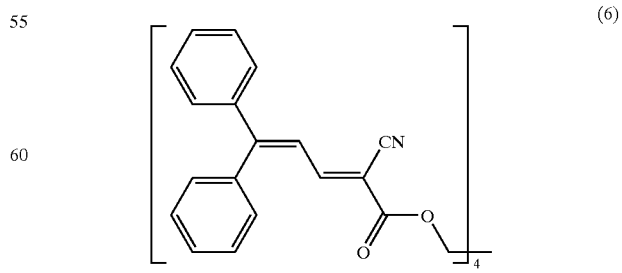

-continued

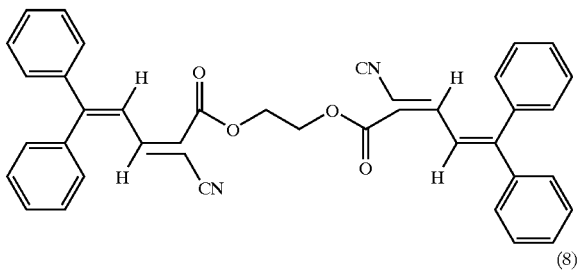
(7)

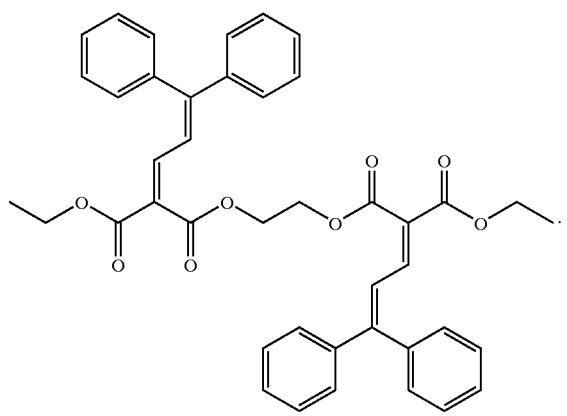
(8)

11. The photostable cosmetic/dermatological composition as defined by claim 1, said at least one dibenzoylmethane compound being selected from the group consisting of:
2-methyldibenzoylmethane,
4-methyldibenzoylmethane,
4-isopropyldibenzoylmethane,
4-tert-butyldibenzoylmethane,
2,4-dimethyldibenzoylmethane,
2,5-dimethyldibenzoylmethane,
4,4'-diisopropyldibenzoylmethane,
4,4'-dimethoxydibenzoylmethane,
4-tert-butyl-4'-methoxydibenzoylmethane,
2-methyl-5-isopropyl-4'-methoxydibenzoylmethane,
2-methyl-5-tert-butyl-4'-methoxydibenzoylmethane,
2,4-dimethyl-4'-methoxydibenzoylmethane,
2,6-dimethyl-4-tert-butyl-4'-methoxydibenzoyl-methane,
and mixtures thereof.

12. The photostable cosmetic/dermatological composition as defined by claim 11, said at least one dibenzoylmethane compound comprising 4-(tert-butyl)-4'-methoxydibenzoyl-methane.

13. The photostable cosmetic/dermatological composition as defined by claim 11, said at least one dibenzoylmethane compound comprising 4-isopropyldibenzoylmethane.

14. The photostable cosmetic/dermatological composition as defined by claim 1, said at least one 4,4-diarylbutadiene compound comprising from 0.5% to 15% by weight thereof.

15. The photostable cosmetic/dermatological composition as defined by claim 14, said at least one 4,4-diarylbutadiene compound comprising from 1% to 10% by weight thereof.

16. The photostable cosmetic/dermatological composition as defined by claim 1, said at least one dibenzoylmethane compound comprising from 0.5% to 15% by weight thereof.

17. The photostable cosmetic/dermatological composition as defined by claim 16, said at least one dibenzoylmethane compound comprising from 1% to 10% by weight thereof.

18. The photostable cosmetic/dermatological composition as defined by claim 1, further comprising at least one other UV-A-active and/or UV-B-active organic screening agent other than a cinnamate sunscreen.

19. The photostable cosmetic/dermatological composition as defined by claim 18, said at least one other organic UV-screening agent being selected from the group consisting of anthranilates; salicylic derivatives; camphor derivatives; benzophenone derivatives; β,β'-diphenylacrylate derivatives; benzotriazole derivatives; benzalmalonate derivatives; benzimidazole derivatives; imidazolines; bis-benzazolyl derivatives; p-aminobenzoic acid (PABA) derivatives; methylenebis(hydroxyphenyl)benzotriazole derivatives; screening polymers and screening silicones; dimers derived from α-alkylstyrene and mixtures thereof.

20. The photostable cosmetic/dermatological composition as defined by claim 19, said at least one other organic UV-screening agent being selected from the group consisting of:
Ethylhexyl salicylate,
Octocrylene,
Phenylbenzimidazole sulfonic acid,
Terephthalylidenedicamphorsulfonic acid,
Benzophenone-3,
Benzophenone-4,
Benzophenone-5,
4-Methylbenzylidenecamphor,
Disodium phenyl dibenzimidazole tetrasulfonate,
Anisotriazine,
Ethylhexyl triazone,
Diethylhexyl butamido triazone,
2,4,6-tris(Diisobutyl 4'-aminobenzalmalonate)-s-triazine,
Methylenebis(benzotriazolyl)tetramethylbutyl-phenol,
Drometrizole trisiloxane, and mixtures thereof.

21. The photostable cosmetic/dermatological composition as defined by claim 1, further comprising at least one UV-screening coated or uncoated metal oxide pigment or nanopigment.

22. The photostable cosmetic/dermatological composition as defined by claim 21, said at least one UV-screening pigment or nanopigment comprising titanium oxide, zinc oxide, iron oxide, zirconium oxide, cerium oxide, and mixtures thereof.

23. The photostable cosmetic/dermatological composition as defined by claim 1, further comprising at least one agent for artificially tanning and/or browning the skin.

24. The photostable cosmetic/dermatological composition as defined by claim 1, further comprising at least one adjuvant or additive selected from the group consisting of fatty substances, organic solvents, ionic or nonionic thickeners, softeners, antioxidants, free-radical scavengers, opacifiers, stabilizers, emollients, silicones, α-hydroxy acids, antifoams, moisturizers, vitamins, insect repellants, fragrances, preservatives, surfactants, anti-inflammatories, substance P antagonists, fillers, polymers, propellants, acidifying or basifying agents, colorants, and mixtures thereof.

25. The photostable cosmetic/dermatological composition as defined by claim 1, formulated for photoprotecting the human epidermis and comprising a nonionic vesicular dispersion, an emulsion, a cream, a milk, a gel, a cream-gel, a suspension, a dispersion, a powder, a solid, a mousse or a spray.

26. The photostable cosmetic/dermatological composition as defined by claim 1, formulated as a makeup for the eyelashes, the eyebrows or the skin and comprising a solid or pasty, anhydrous or aqueous formulation, or an emulsion, a suspension or a dispersion.

27. The photostable cosmetic/dermatological composition as defined by claim 1, formulated for photoprotecting the hair against ultraviolet rays and comprising a shampoo, a lotion, a gel, an emulsion or a nonionic vesicular dispersion.

28. A regime or regimen for photoprotecting the skin and/or hair against the damaging effects of UV radiation, comprising topically applying thereon an effective amount of the photostable cosmetic/dermatological composition as defined by claim 1.

29. A method for enhancing the UV photostability of a photolabile dibenzoylmethane sunscreen compound, comprising formulating therewith an effective amount of at least one 4,4-diarylbutadiene compound in a weight ratio of 4,4-diarylbutadiene compound to dibenzoylmethane sunscreen compound of greater than 2.5 and in the absence of a cinnamate sunscreen.

* * * * *